United States Patent
Valois et al.

(10) Patent No.: US 12,193,952 B2
(45) Date of Patent: Jan. 14, 2025

(54) PROSTHETIC LINER AND METHOD FOR MAKING THE SAME

(71) Applicant: Ossur Iceland ehf, Reykjavik (IS)

(72) Inventors: Christophe Valois, Reykjavik (IS); Linda Ros Birgisdottir, Reykjavik (IS); Sigurdur Asgeirsson, Foothill Ranch, CA (US); Stefan Orn Kristjansson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 18/336,467

(22) Filed: Jun. 16, 2023

(65) Prior Publication Data

US 2023/0320875 A1   Oct. 12, 2023

Related U.S. Application Data

(63) Continuation of application No. 16/704,419, filed on Dec. 5, 2019, now Pat. No. 11,730,612.
(Continued)

(51) Int. Cl.
*A61F 2/78* (2006.01)
*D04B 1/26* (2006.01)
*D06M 15/643* (2006.01)

(52) U.S. Cl.
CPC ............ *A61F 2/7812* (2013.01); *D04B 1/265* (2013.01); *D06M 15/643* (2013.01); *D10B 2403/0331* (2013.01)

(58) Field of Classification Search
None
See application file for complete search history.

(56) References Cited

U.S. PATENT DOCUMENTS

| 4,733,545 A * | 3/1988 | Weinle | D04B 21/18 66/193 |
| 4,923,474 A | 5/1990 | Klasson et al. | |

(Continued)

FOREIGN PATENT DOCUMENTS

WO    2018208588 A1    11/2018

OTHER PUBLICATIONS

Chiu et al., "Curing Behavior, Mechanical Properties, Intermolecular Interaction, and Morphology of Silicone/Polypyrrole/Polymer Electrolyte Composites," Journal of Applied Polymer Science, vol. 101, 2006, pp. 2754-5764.

(Continued)

*Primary Examiner* — Alexander M Weddle
(74) *Attorney, Agent, or Firm* — Workman Nydegger

(57) ABSTRACT

A method for making a prosthetic liner includes the steps of providing a textile sleeve, applying an uncured silicone material onto an inner surface of the textile sleeve and impregnating interstices of a high-density knit structure of the textile sleeve. The silicone material is a fast-cure silicone material arranged to reach at least 90% cross-linking faster than conventional silicone material. The silicone material is preferably limited to the inner surface of the textile sleeve, whereas the outer surface is devoid of the silicone material. The silicone defines an inner layer forming the interior surface of the liner, and the outer surface of the textile sleeve forms the exterior surface of the liner. A thickness of the liner from the interior surface of the liner to the inner surface of textile layer consists of the silicone of the inner layer.

16 Claims, 8 Drawing Sheets

Related U.S. Application Data

(60) Provisional application No. 62/775,611, filed on Dec. 5, 2018.

(56) References Cited

U.S. PATENT DOCUMENTS

| | | | |
|---|---|---|---|
| 5,376,129 | A | 12/1994 | Faulkner et al. |
| 5,507,834 | A | 4/1996 | Laghi |
| 6,136,039 | A * | 10/2000 | Kristinsson ............ A61F 2/7812 623/36 |
| 6,485,776 | B2 | 11/2002 | Janusson et al. |
| 7,611,998 | B2 | 11/2009 | Jackson et al. |
| 8,070,828 | B2 | 12/2011 | Shannon |
| 9,358,138 | B2 | 6/2016 | Kelley et al. |
| 10,271,968 | B2 | 4/2019 | Bache et al. |
| 2001/0039159 | A1 * | 11/2001 | Janusson ............... B29C 70/467 442/306 |
| 2002/0002405 | A1 * | 1/2002 | Janusson .............. B29D 23/001 623/36 |
| 2007/0043450 | A1 * | 2/2007 | Pickering .................. A61F 2/78 623/36 |
| 2011/0208321 | A1 * | 8/2011 | Doddroe ............... A61F 2/7812 623/36 |
| 2014/0076484 | A1 | 3/2014 | Bjarnason et al. |
| 2014/0249650 | A1 * | 9/2014 | Laghi ..................... D04B 35/36 28/142 |
| 2015/0142133 | A1 * | 5/2015 | Egilsson ................... A61F 2/80 623/36 |
| 2017/0008210 | A1 * | 1/2017 | Koellnberger ........... C08J 7/042 |
| 2017/0239070 | A1 | 8/2017 | Walter |
| 2019/0183664 | A1 | 6/2019 | Asgeirsson et al. |

OTHER PUBLICATIONS

Ray, "Fundamentals and Advances in Knitting Technology," Woodhead Publishing India Pvt. Ltd., 2012, 17 pages.

Au, "Advances in Knitting Technology," Woodhead Publishing Limited, No. 89, 2011, 24 pages.

Fawcett et al., "Rapid, Metal-Free Room Temperature Vulcanization Produces Silicone Elastomers," Journal of Polymer Science, Part A: Polymer Chemistry, Issue 51, 2013, pp. 644-652.

* cited by examiner

PROSTHETIC LINER AND METHOD FOR MAKING THE SAME

BACKGROUND

A prosthetic liner is a protective cover adapted to reduce movement and chafing between the skin of a residual limb and a hard prosthetic socket. Prosthetic liners are typically made from a flexible cushioning material and may include an inner portion or layer formed from a polymeric material. The polymeric material may serve as a cushioning material to offer stability and adhesion to soft-tissue of a limb. An outer cover may be provided in the form of a textile layer upon and/or to which the polymeric material or layer secures.

Polymeric materials, preferably including elastomeric materials such as silicone, are a highly desirable material for manufacturing numerous medical and consumer products, including prosthetic liners, in part due to such materials being soft to the touch but resistant to pressure. Polymeric or elastomeric materials may be adapted to have frictional properties to resist movement and migration on a limb. As prosthetic liners interface between a residual limb of a user and the hard load-bearing socket of a prosthetic attachment, the durability, comfort, and cost of polymers are advantageous. Polymeric materials, including elastomeric materials, are also conveniently shaped into precise dimensions, making polymeric materials an ideal choice for prosthetic liners.

Prosthetic liners formed from elastomeric materials are described in prior patents, such as, for example, U.S. Pat. No. 4,923,474 issued May 8, 1990; U.S. Pat. No. 5,507,834 granted Apr. 16, 1996; U.S. Pat. No. 5,376,129 granted Dec. 27, 1994; U.S. Pat. No. 6,485,776, granted Nov. 26, 2002; U.S. Pat. No. 9,770,891, granted Sep. 26, 2017; and U.S. Patent Application Publication no. 2019/0183664, published Jun. 20, 2019; each of these patents or publications are incorporated herein. Elastomeric liners are used to cushion a post-operative stump or residual limb regarding a prosthesis installed over the residual limb and coupled to the socket by a locking element as described in U.S. Pat. No. 5,376,129. The suspension of the prosthesis may also occur due to the suction of the liner against the residual limb, as described in U.S. Pat. No. 5,718,925, granted Feb. 17, 1998, incorporated herein by reference.

As an exemplary example or species of elastomer, silicone products are ordinarily formed by providing an uncured silicone material in a liquid or semi-liquid form and then curing the silicone material within a set of molds, such that the cured silicone assumes the desired shape, as taught in U.S. Pat. No. 6,485,776. Curing processes may involve the use of different catalysts, crosslinking agents, cure inhibitors, and accelerators. Other additives may be added to influence the durometer of the silicone liner and/or to provide other desired properties, such as skin-beneficial properties. The viscosity of the uncured silicone material may further be varied in order to effect the desired cure rate in cooperation with a textile layer and its properties.

When producing a prosthetic liner, a textile layer may be provided on an exterior, or outward-facing surface of an inner layer (whereas the interior, or inward-facing surface of the inner layer contacts a user's skin directly). The textile layer beneficially imparts desired surface and mechanical properties, such as texture, shape, and breathability, and may further interface with a socket or other prosthetic attachment. To reliably attach the inner layer to the textile layer, the uncured silicone material is cured against an inner surface of the textile layer such that the cured silicone attaches to and impregnates a portion of the textile layer.

Because an uncured silicone material is often a viscous or semi-viscous liquid, and due to the time required to cure the uncured silicone material, there is a problem of uncured silicone material bleeding through an entirety of a thickness of the textile and extending to an opposed, outer surface of the textile layer. This can defeat the purpose of the textile layer or interfere with the proper functioning of the textile layer or the liner as a whole and may be difficult to handle.

To address the problem of unwanted "bleed-through," existing prosthetic liners are produced in a costly, cumbersome, and time-consuming process of coating or pre-coating an interior surface of a textile material, often a tubular textile, with a separate inner layer or film, which prevents the uncured silicone material from bleeding through the textile layer and interfering with desired functional properties of the prosthetic liner. Referring to U.S. Pat. No. 6,485,776, the coating step requires that the textile layer be a tubular textile structure of uniform dimensions such that the coating process is expedited and achieves a reliable coating over a surface of the textile layer, whether along a segment or an entirety of the liner. The coating step further requires that uncured silicone material be separately mixed and prepared for the coating or film layer in addition to the uncured silicone material that is provided for the inner layer.

After the coating step, the tubular textile structure (which may be provided on a roll) is cut, shaped, and stitched (or otherwise attached) into the desired configuration suitable for the prosthetic liner, compounding the costs and complexity of the manufacturing process. For example, a distal end must be formed on the tubular textile structure by stitching, gluing, or other suitable processes. Because the coating process often requires a tubular textile, the tubular textile structure may not provide individual, discrete areas along its surface relative to its axis with different knit structures, materials, properties, or shapes corresponding to areas of the prosthetic liner that may benefit from a specific property.

Such properties might be different stiffness according to proximity to portions of a residual limb and a corresponding socket. Such features may be added by assembling through shaping and stitching multiple portions of different materials and adhering them together, further adding to the costs of the liner-manufacturing process.

According to prior art methods, a tubular textile is typically open at both ends to enable and facilitate the coating process, which precludes the use of customized textile socks for a prosthetic liner. Textile socks, in contrast to tubular textile structures, may be pre-formed and may have many discrete sections, knit structures, materials, properties, and shapes, all of which may provide certain structural and functional benefits to a user in desired regions, and may not require the separate cutting, shaping, and stitching efforts required to form a tubular textile structure after coating into the specific configuration required of a prosthetic liner.

Because of the existing state of elastomer-curing processes, bleed-through of the uncured silicone material remains a problem that precludes the use of pre-formed and/or custom textile sleeves, socks, or other products and increases the costs and complexities of manufacturing. For at least the foregoing reasons, there is a need for an improved prosthetic liner and method of manufacturing the same that overcomes the challenges of existing elastomeric prosthetic liners by eliminating the coating requirement and enabling the use of improved textile layers, such as textile sleeves or socks.

SUMMARY

The problem of uncured silicone material and other elastomeric materials bleeding through a textile layer, from an inner side to an outer side, in a prosthetic liner manufacturing process is addressed by providing a prosthetic liner according to embodiments of the present disclosure including a fast-cure silicone material and a textile layer configured to prevent bleed-through of the uncured silicone material. By providing both a fast-cure silicone material and a configured textile layer arranged to cooperate with the fast-cure silicone material, the need for a coating process to prevent bleed-through is obviated, as is the need to use tubular textile structures that limit the structure and function of prosthetic liners while increasing the costs and complexities of the liner-manufacturing process.

In an embodiment, an inner layer is formed on a textile layer to define a prosthetic liner comprising a distal portion opposite a proximal portion, and a body portion defined between the distal and proximal portions. The prosthetic liner defines an open proximal end and a closed distal end suitable for surrounding a limb residuum for insertion into a prosthetic socket. An exterior surface of the prosthetic liner is defined by a textile layer in the form of a textile sleeve or sock, with an interior surface of the prosthetic liner defined by an inner layer attached to the textile sleeve.

The inner layer is arranged as being a fast-cure silicone material by the provision of an uncured silicone material mixture comprising silicone functional polymers, a catalyst, and a crosslinking agent. The catalyst and crosslinking agent are provided in sufficient quantities to rapidly cure or "fast-cure" the silicone functional polymers into a solid inner layer while adhering the inner layer to the surface of the textile sleeve without bleeding through an entirety of a thickness of the textile sleeve to an outer surface of the liner. A non-limiting example of a catalyst is a platinum-based catalyst. A non-limiting example of a silicone functional polymer is a vinyl functional siloxane polymer. A non-limiting example of a crosslinking agent is a hydride functional siloxane polymer. Other catalysts, silicone functional polymers, and crosslinking agents may be provided as suitable.

The uncured silicone material may be provided in two parts, with the catalyst and the crosslinking agent provided in separate parts that are mixed prior to curing. The uncured silicone is further configured to provide superior qualities such as desired durometer and tensile force, material stability, proper coloration, and desired mechanical properties like tackiness relative to existing or conventional prosthetic liners.

The textile sleeve comprises at least a first knit structure and a material configured to cooperate with the fast-cure silicone material to prevent bleed-through of the uncured silicone material, such that no separate coating is required, and to provide superior mechanical properties, such as elasticity. The textile material has a "high-density" knit structure, as measured by a knitting machine gauge, in a preferable range of 16 to 26, to prevent unwanted bleed-through of the fast-cure silicone material. The textile sleeve may comprise discrete portions of different materials, knitted patterns, and other properties unavailable in tubular textile materials used in existing prosthetic liners, which have uniform properties. The textile sleeve may be provided in a pre-formed configuration, such that no cutting, shaping, or stitching operations are required to produce the prosthetic liner or before the curing step.

By providing a combination of a fast-cure silicone material and a cooperating textile material or sleeve according to embodiments of the disclosure, multiple processing steps used to manufacture existing prosthetic liners may be entirely omitted. Because there is no need for a separate coating procedure, a separate polymer pre-mixing stage is eliminated, as is the coating process itself. Because the textile sleeve may be pre-formed, the steps of cutting a coated tubular textile material, sewing said material, and/or gluing or otherwise stitching the material into specific shapes may be further omitted. Regarding the term "pre-formed," the textile sleeve may be pre-configured or comprise predetermined properties to be ready to receive uncured silicone material without shaping, cutting, stitching, or pre-coating stages. The procedure for manufacturing a prosthetic liner is thus advantageously reduced to a single molding step, which occurs faster than in conventional processes.

While silicone is provided as an exemplary polymer, other polymers may be provided. For example, elastomeric polymers such as polyisoprene, polybutadiene, polychloroprene, butyl rubber, styrene rubber, nitrile rubber, ethylene propylene rubber, polyacrylic rubber, polyamides, fluoroelastomers and perfluoroelastomers, polyether block amides, ethylene-vinyl acetate, polyolefin elastomers, polyurethanes, copolyesters, copolymers or block copolymers of different polymers, or any other suitable polymeric material may be used.

In other embodiments of the disclosure, a textile layer or sleeve may advantageously provide features unavailable to existing or conventional prosthetic liners due to the need to coat and shape a uniform tubular textile structure prior to curing an inner layer onto the coated textile. For example, the textile sleeve according to embodiments of the disclosure may comprise an integrated matrix of thermofusible yarn. The thermofusible yarn is provided to impart added stiffness, particularly in axial directions. The stiffness and other properties of the thermofusible yarn may further define certain shapes in the textile sleeve, such as at the distal portion to better conform to the limb or the socket, and to help prevent wrinkles or unwanted folding.

Whereas in existing or conventional liner-manufacturing processes a matrix of thermofusible yarns must be added to a tubular textile structure after a coating procedure, the textile sleeve or sock of embodiments of the disclosure may advantageously be provided with the thermofusible yarns or matrix, further reducing the costs and complexities of the manufacturing process. The thermofusible yarns may be formed from any suitable material, including synthetic materials such as polyesters, polyamides, nylons, or any other suitable material. The thermofusible yarns may comprise a material that melts at a desired temperature in order to bond the thermofusible yarns to adjacent yarns, fibers, or other materials.

The thermofusible yarns according to the disclosure may be configured to be fused prior to molding, and may be molded to a shape of the distal end portion of the textile sock. By fusing the thermofusible yarns prior to molding, the textile sleeve or sock may be fitted to a shape of the molds used in the molding process due to the increased stiffness provided by the thermofusible yarns, and may in this manner fit to the molds without wrinkles or other deformations. Alternatively, the thermofusible yarns may be fused during the molding or curing process of the elastomeric material.

The thermofusible yarns may be selected and configured to fuse at a minimum temperature of approximately 110° C., and preferably between a range of 110° C. and 150° C. The thermofusible yarns may advantageously be integrated with the yarns of the textile layer 102 in desired regions, such as at the distal end portion 108. The thermofusible yarns may be integrated into the knit of the textile layer 102 in such a way as to increase stiffness when bonded in desired directions, such as axially.

The textile layer or sleeve may define discrete regions of non-stretchable and/or coarse stitching to facilitate controlled bleeding-through of uncured silicone material through the thickness of the textile layer at the discrete regions. The discrete regions, for example dots, of material in the textile sleeve may have lighter (e.g. less dense) knitting to facilitate breathability (if the fast-cure silicone material is not arranged to bleed therethrough) or to provide controlled bleed-through of the fast-cure silicone material, so as to provide silicone features on the exterior or socket-facing surface of the prosthetic liner. The discrete regions or dots of material may be provided in patterns and locations for optimized breathability and/or rotation control.

The result of such controlled bleeding-through may be one or more discrete regions of silicone on an outer or socket-facing surface of the prosthetic liner. The discrete regions of silicone may define seal-in bands to facilitate a vacuum seal and a more robust attachment between the prosthetic liner and a corresponding socket, for example. The discrete regions of silicone may also provide rotational control between the liner and the socket and/or stabilization in axial directions.

A textile sleeve may be provided and arranged to cooperate with the fast-cure silicone material to prevent bleed-through of uncured silicone material. The textile sleeve may have regions of low axial stretching to prevent pistoning, particularly proximate a distal end portion of the textile sleeve. Regions of higher axial stretching may be provided proximal to the distal end portion of the textile sleeve. The higher axial stretching regions may facilitate knee flexion, for example. Stiffer regions of the textile sleeve may provide patella support, and patterns or other features comprising softer yarn or predetermined patterns and shapes may be provided to ensure correct folding when the prosthetic liner is bent, for example at a popliteal region of a knee.

According to an exemplary method of the disclosure, a liner for prosthetic use is made according to certain steps. The definitively formed liner or completed product according to the exemplary method will result in an exterior surface and an inner cavity forming an interior surface of the liner. A textile sleeve is provided having a first knit structure with interstices between individual yarns of the first knit structure. The textile sleeve defines an inner surface and an outer surface on an opposite side of the inner surface, and the first knit structure is preferably a high-density knit.

Uncured silicone material is applied onto the inner surface of the textile sleeve and impregnates the interstices defined between individual yarns of the first knit structure of the textile sleeve through at least part of a thickness of the textile sleeve, thereby securely adhering the silicone of the inner layer to the textile layer. The silicone material is preferably a fast-cure silicone material arranged to cure to at least 90% crosslinking within an exemplary range of about 120 to 210 seconds. The impregnation of the silicone material occurs generally only on the inner surface of the textile sleeve so that the outer surface is devoid of the silicone material. The inner layer preferably forms the interior surface of the liner and the outer surface of the textile sleeve forms the exterior surface of the liner without the silicone material completely bleeding through the textile layer. A thickness of the liner from the interior surface of the liner to the inner surface of textile layer consists of the silicone material of the inner layer.

Variations of the aforementioned exemplary method may be provided according to exemplary illustrations and discussions described herein, including additions or omissions of steps to the method, and the use of different polymeric materials or textile layers and/or adaptations thereof.

A definitively formed liner for prosthetic use may be formed according to the method having the aforementioned structure. Variations of the liner or a prosthetic sleeve may also be provided according to exemplary illustrations and discussions described herein.

By utilizing fast-cure silicone material and textile layers configured to cooperate therewith, particularly of a high-density knit structure, pre-formed with predetermined features, the methods for making a prosthetic liner and the prosthetic liner embodiments of the present disclosure address the problem of existing prosthetic liners being costly and complex to produce. The fast-cure silicone material and cooperating textile layers disclosed herein allow for omitting a coating procedure and facilitate the use of pre-formed textile sleeves in place of uniform tubular textile structures, providing for additional structures that provide enhanced shape and other properties to the prosthetic liner and reduce the costs and complexities of existing manufacturing processes.

These and other features of the disclosure will become better understood regarding these description, appended claims, and accompanying drawings.

Figure 1A:
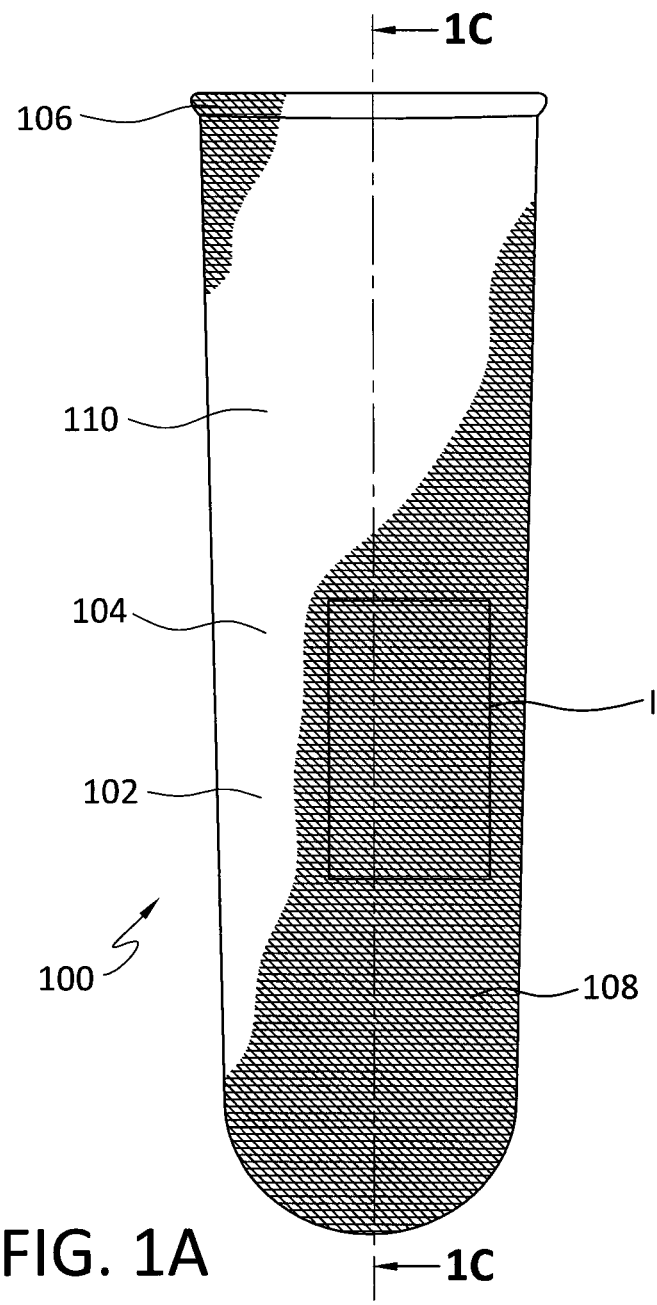
FIG. 1A is an elevational view of a prosthetic liner according to an embodiment of the disclosure.

The drawing figures are not necessarily drawn to scale, but instead are drawn to provide a better understanding of the components, and are not intended to be limiting in scope, but to provide exemplary illustrations. The figures illustrate exemplary configurations of a prosthetic liner, and in no way limit the structures or configurations of a prosthetic liner according to the present disclosure.

DETAILED DESCRIPTION OF VARIOUS EMBODIMENTS

According to embodiments of the disclosure, the provision of an elastomer, such as a silicone material, having fast-cure properties in cooperation with a textile layer arranged to prevent unwanted bleed-through of uncured elastomeric material advantageously simplify manufacturing processes for prosthetic liners by omitting a pre-coating stage and by facilitating the use of pre-formed textile sleeves or socks. The fast-cure properties of a silicone material are compared to curing properties of a conventional silicone material having slower cross-linking properties, measured in time as a function to reach at least 90% cross-linking of originally uncured silicone material.

Preferably, the textile material has a high-density knit structure, as measured by a kitting machine gauge in an exemplary range of 16 to 26, to prevent unwanted bleed-through in combination with the fast-cure silicone material. The fast-cure silicone material and textile layer in cooperation therewith also allows for the use of pre-formed textile sleeves or socks having numerous advantageous features, regions, and patterns of textile material, as these textile sleeves do not require the numerous pre-coating, cutting, shaping, and stitching steps required by existing textile layers in prosthetic liners.

"Silicone," as used herein, is used generally to denote a cured silicone or elastomeric material, preferably a silicone that was configured to cure more rapidly than conventional silicone materials, whereas "silicone material," or "fast-cure silicone material," as used herein, are used generally to denote an as-yet uncured silicone material.

Discussions on the relationship between knitting machine gauge and yarn count can be found in Chapter 18.16, "Yarn and its selection for knitting," in Fundamentals and Advances in Knitting Technology, by Sandhan Chandra Roy, 2012; Chapter 9, "Quality control in the knitting process and common knitting faults," in Advances in Knitting Technology, edited by K. F. Au, 2011; each of which is incorporated by reference.

Figure 1B:
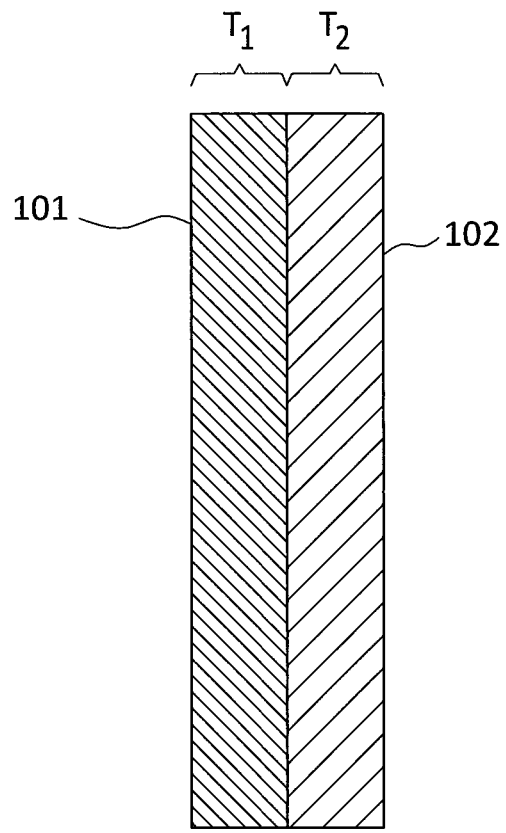
FIG. 1B is a cross-sectional view of the prosthetic liner of FIG. 1A taken along the line 1C-1C.
Figure 1C:
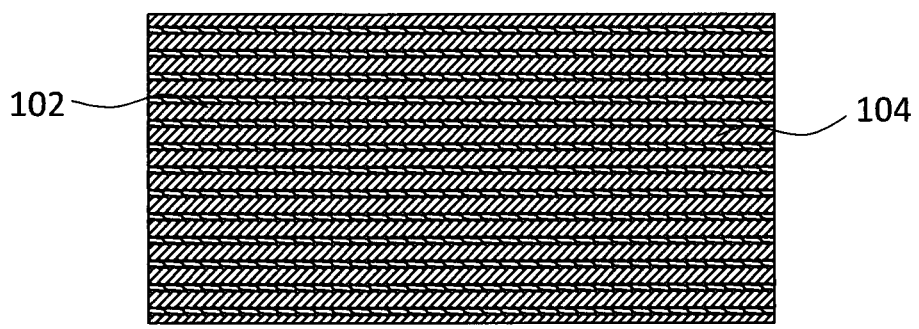
FIG. 1C is a detail view I of a textile material in the prosthetic liner of FIG. 1A.

As shown in FIGS. 1A-1C, a prosthetic liner 100 comprises an inner layer 101 which may be formed from a polymeric or elastomeric material (in the exemplary form of silicone) and an outer textile layer 102 adjacent to the inner layer 101. The inner layer 101 is arranged to define an inner cavity and to be adjacent to a user's limb residuum while the textile layer 102 is arranged to contact a prosthetic socket or other attachment. The prosthetic liner 100 may define a proximal portion 106 and a distal portion 108 distinct from and/or defining a body portion 110 extending between the proximal portion 106 and the distal portion 108. The distal portion 108 may define a shape configured for attachment to a corresponding prosthetic socket. The body portion 110 is arranged to contact a length of a user's limb residuum at least corresponding to a length of the prosthetic socket or attachment.

The inner layer 101 may be formed directly on the textile layer 102 from a fast-cure silicone material comprising at least a silicone functional polymer, a catalyst, and a cross-linking agent. The silicone functional polymer may comprise one or more functional polymers arranged to be polymerized or crosslinked by the catalyst and the cross-linking agent to form a solid silicone structure with desired properties, including durometer and tensile force. The silicone functional polymer may comprise vinyl functional silicones comprising functional groups lending desired properties to the silicone liner 100, or any arrangement or combination of functional polymers suitable for forming a prosthetic liner.

The fast-cure silicone material may further have a viscosity configured to enable fast-cure of the silicone material without bleed-through, as it has been found that a higher viscosity of the uncured silicone material slows the rate at which the silicone material impregnates the interstices between individual yarns of the textile layer. This facilitates curing of the silicone material before the silicone material penetrates an entirety of a thickness of the textile layer.

To form the inner layer 101, the uncured silicone material is added to a mold and disposed against a surface, preferably an inner surface, of the textile layer 102, allowing the silicone functional polymer to form a solid inner layer 101 attached to the textile layer 102, by action of the catalyst and crosslinking agent forming polymeric bonds and attachments among the silicone functional polymer. Heat or UV radiation may be added or used to expedite the curing process. In embodiments, a male mold and a corresponding female mold may be provided. The textile layer, sleeve, or sock may be placed on the male mold, and the male mold is then inserted into the female mold. The male and female molds may be configured to correspond to a particular user's limb residuum, thereby producing a prosthetic liner closely corresponding to the user's dimensions and needs. In other embodiments, the male and female molds may correspond to a general or off-the-shelf shape or size.

A distance may be defined between the textile layer on the male mold and the female mold when the male mold and the female mold are engaged, the distance corresponding to a desired thickness of the inner layer 101. The uncured silicone material may be introduced to the distance between the male and female molds and then cured therebetween such that the inner layer 101 assumes a configured corresponding to the distance defined by the molds and cures against a surface of the textile layer. To expedite or control the rate of curing, one or both of the male and female molds may be heated by any suitable heating element or heat source, or may be cooled by any suitable heat-transfer element. The temperature of the molds may be controlled or regulated in any suitable manner so as to control the rate of curing. The described embodiment is merely exemplary, and any suitable means may be used to cure the silicone material against a surface of the textile.

In embodiments of the present disclosure, the fast-cure silicone material may comprise silicone functional polymer, catalyst, and crosslinking agent in sufficient quantities to cure or polymerize the silicone functional polymer into a solid inner layer at an expedited rate and without compromising the qualities of the inner layer, such that bleed-through is prevented. The rate of polymerization is proportional to the quantities of catalyst and crosslinking agent, but excessive quantities of catalyst and crosslinking agent may cause reduced inner layer quality. For instance, excessive quantities of catalyst may adversely affect the stability of the inner layer and may discolor the silicone. Excessive quantities of crosslinking agent may reduce or adversely affect mechanical properties and make the final inner layer too tacky to the touch.

The fast-cure silicone material forming the inner layer 101 may have predetermined quantities of silicone functional polymer, catalyst, and crosslinking agent to create an expedited curing process without reducing the quality of the inner layer 101 relative to existing or conventional elastomeric prosthetic liners. The inner layer 101 may be cured according to other optimized factors, including the heat provided at the mold. In embodiments, the inner layer 101 may have a durometer gauge OO in a range from about 20 to about 60, and preferably about 30 to about 36, and a tensile force at 100% elongation of about 0.5 N to about 5 N, and preferably about 0.95 N to about 1.81 N.

Existing processes for curing silicone typically have a cure time, as a condition at which the functional polymer of the uncured silicone is 90% crosslinked, ranging from 8-10 minutes for the silicone to cure, and forming an inner layer with a thickness ranging from about 1 mm proximate a proximal end of the liner to about 15 mm proximate a distal end of the liner. The fast-cure silicone material of the disclosure advantageously provides a faster cure time, and hence "fast-cure," ranging from generally about 1 minute or 60 seconds to about 10 minutes or 600 seconds, preferably about 2 minutes or 120 seconds to about 6 minutes or 360 seconds, and more preferably about 2.5 minutes or 150 seconds to about 3 minutes or 180 seconds; or any combination of low and high of the aforementioned range. Accordingly, a preferred range is 150 to 210 seconds. This shortened or "fast-cure" time allows for the fast-cure silicone material to form an inner layer directly on the textile without bleeding through the textile layer as occurs in existing processes. This allows for the omission of a pre-coating process which aims to prevent bleed-through. This example is at least one manner in which "fast curing" may be characterized and does not limit other manners.

In contradistinction to the fast-cure silicone material of this disclosure, thereby forming the definitive silicone inner layer of the liner according to this disclosure, in U.S. Pat. No. 6,485,776 a cure time of about 6 minutes is required, and such cure time is in combination with the already-formed coating on the innermost layer of the fabric or textile layer. U.S. Patent Application Publication no. 2010/0016993, published Jan. 21, 2010, incorporated herein by reference, describes a cure time for certain silicone components of as much as one hour. Similarly, U.S. Patent Application Publication no. 2004/0137178, published Jul. 15, 2004, incorporated herein by reference, describes a cure time of 50 minutes.

The fast-cure silicone material forming the inner layer 101 may be further arranged with quantities and selections of silicone functional polymer, catalyst, and/or crosslinking agent to form an inner layer 101 in combination and cooperation with a textile layer 102. The silicone and textile layers 101, 102 form a liner 100 having an axial percent elongation at 25N of about 20 to about 150, preferably about 60 to about 150, and a radial percent elongation at 25N of about 10 to about 150, preferably about 70 to about 135. The inner layer 101 and the textile layer 102 of the liner 100 may further be arranged such that the liner 100 has an axial force at 30% elongation of about 0 N to about 10 N, preferably about 3.5 N to about 6.5 N, and a radial force at 30% elongation of about 2 N to about 8 N, preferably 2.8 N to about 6.5 N. Other properties and other configurations of the prosthetic liner are envisioned.

In embodiments, the fast-cure silicone material is arranged to cooperate with the textile layer 102 so as to form the inner layer 101 with none of the silicone functional polymer, catalyst, or crosslinking agent bleeding through an entirety of a thickness of the textile layer 102. Advantageously, the inner layer 101 may attach to a surface, preferably an interior or user-facing surface, of the textile layer 102 by impregnating interstices defined between certain fibers and individual threads of the textile layer 102 during the curing and polymerization process, without compromising the qualities of the textile layer 102 on its outer or socket-facing surface.

In certain embodiments, the fast-cure silicone material may be an addition-cured silicone preparation from Nusil Technology LLC of Carpinteria, California, and may be provided in two parts, "part A" and "part B." Part A may comprise vinyl functional silicones and the catalyst, while Part B comprises vinyl functional polymer, crosslinking agent, and a cure inhibitor arranged to adjust the cure rate of the system. Curing occurs as a silicon-hydrogen bond (provided in a vinyl functional silicone) is added across the unsaturated carbon-carbon double bound of an olefin (provided in a vinyl functional polymer).

The crosslinking agent may comprise a hydrogen-functional crosslinker, such as a Si—H functional crosslinker or any other suitable crosslinking agent, which may facilitate the solidifying attachment between polymers in the inner layer 101. Part A and Part B may be provided in any suitable ratio, including a 1:1 ratio, a 10:1 ratio, or otherwise. The cure inhibitor may operate to adjust the cure rate of the uncured silicone material by influencing a maximal rate of curing, and may be provided in any suitable quantity or proportion.

While silicone is provided as an exemplary species of polymer or elastomer, other species of polymer may be provided to serve as the inner layer 101. For example, other elastomeric polymers such as polyisoprene, polybutadiene, polychloroprene, butyl rubber, styrene rubber, nitrile rubber, ethylene propylene rubber, polyacrylic rubber, polyamides, fluoroelastomers and perfluoroelastomers, polyether block amides, ethylene-vinyl acetate, polyolefin elastomers, polyurethanes, copolyesters, copolymers or block copolymers of different polymers, or any other suitable polymeric material may be used.

The fast-cure silicone material that forms the inner layer 101 is advantageously arranged to cooperate with and attach to a surface of, but not bleed through an entirety of, the textile layer 102. In the embodiment of FIGS. 1A-1C, the textile layer 102 is a textile sleeve, pre-formed in the depicted configuration, with the distal portion 108, the proximal portion 106, and the body portion 110. The use of a textile sleeve for the textile layer 102 is precluded in existing or conventional prosthetic liner manufacturing processes because of the necessity of pre-coating the textile layer of existing liners with a coating or film formed from silicone or other polymeric material that prevents bleed-through of the uncured silicone material, which is not feasible or economical if the textile is already formed into a sleeve or sock with a distal end portion.

The textile layer 102 is advantageously selected specifically to cooperate with the fast-cure silicone forming the inner layer 101. In contrast to the pre-coating, cutting, shaping, and stitching steps of existing processes for manufacturing a prosthetic liner, the textile layer 102 may be a functional textile sleeve or sock advantageously arranged with sufficient knit structures and materials to prevent bleed-through of the fast-cure silicone material and having discrete regions with structures and functionality appropriate for regions of the limb residuum or prosthetic socket requiring, for example, greater flexibility or alternatively increased stiffness, or any other desired property.

In a preferred embodiment, the textile layer 102 comprises pique-knitted yarns of a high knitting machine gauge, for example, the yarns are gauge 24. The higher gauge helps to seal in and slow the impregnation of interstices between the yarns by the uncured silicone material, preventing bleed-through. The body portion 110 of the textile layer 102 may comprise tencel yarn, while a distal end portion 108 may comprise thermal yarns that assist in capturing the shape of the distal end portion 108, preventing wrinkles and unwanted folding.

In another preferred embodiment, the textile layer 102 may comprise a jersey knit of a high knitting-machine gauge, for example gauge 19. The jersey-knit yarns may further comprise a terry knit, with a looped side on one surface, such as the inner surface, of the textile layer 102 to facilitate impregnation of the interstices between yarns of the textile layer 102 by the uncured silicone material. It has been found that providing a textile layer 102 comprising jersey knitting with terry provides improved sealing-in of the silicone material. Terry has also been found to help align the textile layer 102 to a shape or configuration of the male mold, over which the textile layer 102 is placed to facilitate the molding process. A second, opposite surface, such as the outer surface, of the textile layer 102 may be a substantially flat surface compared to the looped surface.

The jersey-knit textile layer 102 may alternatively be provided without terry knitting. It has been found that a textile layer 102 defining jersey knitting without terry provides improved elongation. The textile layer 102 may comprise any suitable material, including synthetic fibers such as bare or covered elastane, taslanized or air-textured yarn, PET, polyamides, nylons, or other synthetic fibers, natural fibers such as cotton, silk, or wool, modified or combined natural fibers such as tencel thread, combinations thereof, or any other suitable material.

The jersey-knit textile layer 102 may comprise a taslanized yarn in the body portion 110, for example a taslanized yarn with a density of about 190 Decitex (dTex). It has been surprisingly found that a taslanized yarn provides improved sealing-in of the uncured silicone material. The textile layer 102 may be steamed prior to disposing the uncured silicone material and curing thereagainst, as it has been found that steaming the textile layer 102 using suitable steaming means increases the density of the textile layer 102, which results in less bleed-through.

In embodiments, the material of the textile layer 102 may be air-textured to configure the interstices between the individual threads or yarns, particularly on an inner side of the textile layer 102, to receive and engage with the silicone material. The jersey-knit textile layer 102 may alternatively comprise a bare elastane material, which has been found to provide improved elongation in both axial and radial directions. In embodiments the elastane of the jersey-knit textile layer 102 may be covered to reduce bleed-through of the silicone material.

By providing the fast-cure silicone material forming the inner layer 101 of the present disclosure, with silicone functional polymer, catalyst, and crosslinking agent provided in amounts that allow an expedited curing process without adversely affecting the material properties, and a cooperating textile material that prevents bleed-through of the uncured silicone material, no pre-coating step is needed to prevent bleed-through of the inner layer 101 through the textile layer 102 as in U.S. Pat. No. 6,485,776. While no pre-coating step is required according to the methods described herein, the general process of molding the inner layer to the textile layer may be adopted from U.S. Pat. No. 6,485,776, with the modification of skipping the pre-coating step by using the fast-cure silicone material and high-density knit textile layer.

Rather, the inner layer 101 may be formed directly on the textile layer 102 in a greatly simplified process compared to existing manufacturing methods for prosthetic liners. The combination of a fast-cure silicone material forming inner layer 101 and a textile layer 102 arranged to cooperate with the fast-cure silicone material to prevent bleed-through allows for a simplified manufacturing process and for using advantageous textile layers.

In embodiments of the present disclosure, the textile layer 102 may comprise a knit structure arranged to provide optimal sealing of and cooperation with the fast-cure silicone material without compromising textile qualities relative to existing or conventional textile layers. The knit structure may be selected to have optimal or maximal sealing of the fast-cure silicone material while retaining a desired elongation.

The textile layer 102 comprises a textile material 104 that may additionally define parameters and properties that further cooperate with the fast-cure silicone material to prevent bleed-through without compromising the performance or comfort of the textile layer 102. The textile layer 102 or the textile material 104 may comprise a jersey knit structure, which has been found to minimize or prevent entirely bleed-through of the fast-cure silicone material and may comprise stretchy single-knit fabric. The jersey knit structure of the textile layer 102 may be modified with terry toweling or fabric with long and/or cross loop structures with interstices between the yarns while increasing the absorptivity of the fabric to further minimize bleed-through. In other embodiments, the jersey knit structure may omit terry toweling. In yet other embodiments, the textile layer 102 may comprise a pique knit structure.

In embodiments, the textile layer 102 may have increased density compared to existing textile layers, the higher density further preventing bleed-through. To increase the density, the material or yarn forming the textile layer 102 may have increased thickness or knitting machine gauge relative to existing textiles. The material of the textile layer 102 may be roughened, for example with a brush, to prevent bleed-through; this may provide additional surface area for a locking effect between the fast-cure silicone material and the textile layer 102, and to distribute the fast-cure silicone material during the curing process. The textile layer 102 may comprise a material with taslanized or air-textured yarn, bare elastane yarn, covered elastane yarn, tencel yarn, cotton, nylon, polyester, polyamide, or any other suitable material.

In embodiments, a variable-durometer liner may be provided by adding an uncured silicone material comprising a variable number of durometer-dependent components such as oil at specific locations to a mold through a dynamic mixer and extrusion die prior to molding. The base materials that form an uncured silicone material, such as functional silicone polymer, crosslinking agents, catalyst, additives, and durometer-affecting components like oils may be blended together using the dynamic mixer, with a servo motor controlling the dosing of the blended materials. The extrusion die may be positioned using the servo motor to extrude the blended material at designated positions relative to a textile sleeve or sock, with the proportions of the base materials varying based on the location of the textile sock. Because a percentage of oil in the uncured silicone material is proportional to the final durometer, the content of oil in the uncured silicone material may be controlled to increase or decrease the durometer at chosen locations of the inner layer 101.

In other embodiments, the type of polymer, crosslinking agents, or other base materials may be varied to effect desired changes in the durometer or other properties, such as stretch. The locations and proportions of oil or other durometer-affecting components may be chosen based on a desired property relative to the user. For example, a lower durometer may be desired proximate a distal end portion to cushion the limb residuum against the prosthetic socket. A higher durometer may be desired at portions of the prosthetic liner that contact various components of the prosthetic socket for rotation control or other benefits.

The durometer, stretch, or any other suitable property, such as elongation, tear strength, and others, of the inner layer 101 may correspond to and cooperate with properties of the textile sleeve 102 at corresponding locations. The textile sleeve 102 may be provided with similarly adjusted thickness, stretch, elongation, or other properties as appropriate.

Figure 1D:
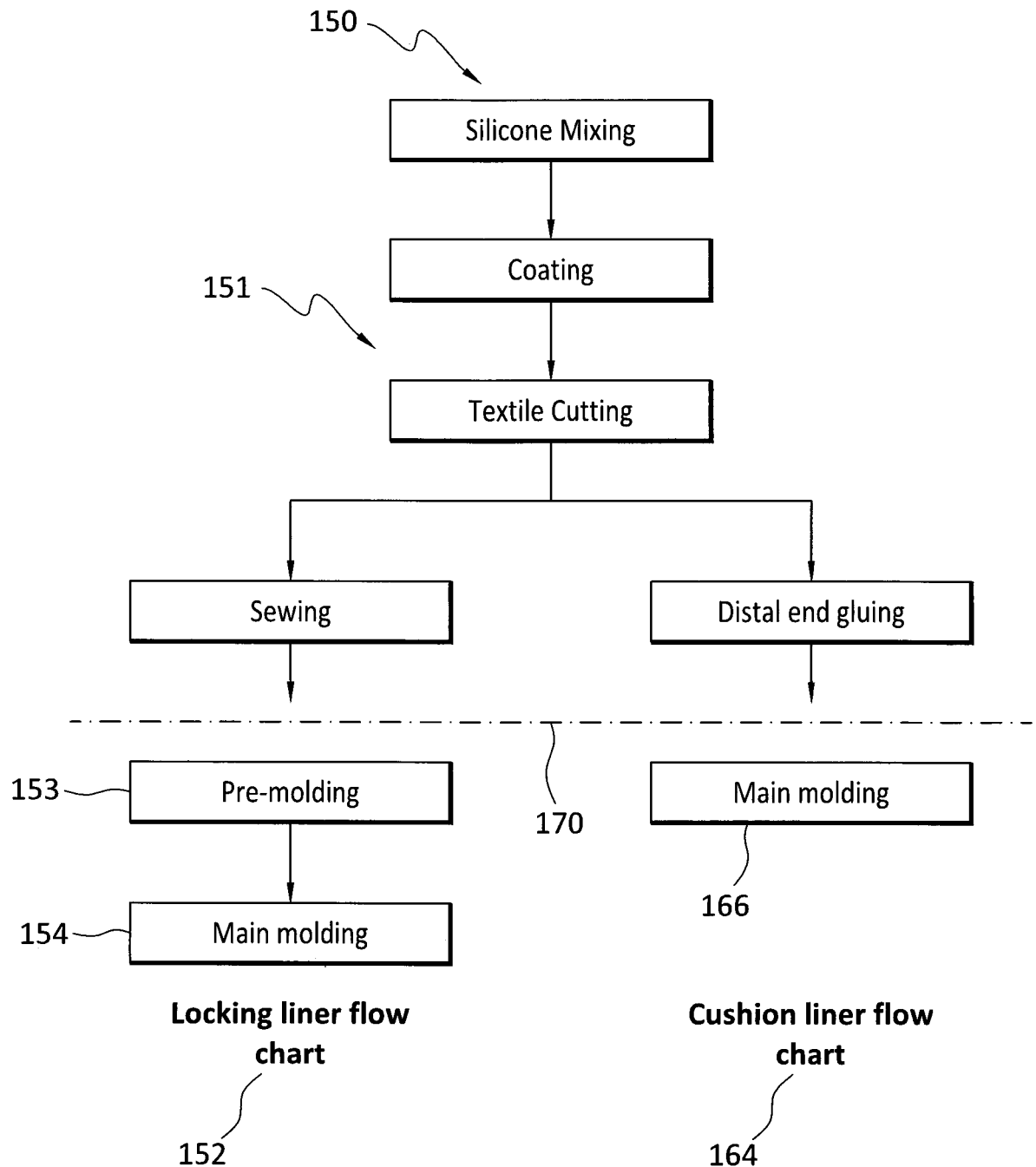
FIG. 1D is a flowchart showing an existing manufacturing process for prosthetic liners versus the manufacturing process enabled by embodiments of the disclosure.

FIG. 1D shows a flowchart 150 describing an existing process for manufacturing a prosthetic liner, with a coating or pre-molding process 151 comprising the steps of: mixing silicone, coating a tubular textile material with the mixed silicone to prevent bleed-through during the molding process, and cutting textile to form the coated tubular textile material into a configuration suitable for a textile layer of a prosthetic liner. Depending on whether the prosthetic liner is destined for use as a cushion liner or a locking liner (two potential dispositions for a prosthetic liner), the coating or pre-molding process 151 further comprises the steps of distal end gluing or sewing, respectively, to further form the coated tubular textile material into a configuration usable as a textile layer of a prosthetic liner.

FIG. 1D further shows a locking liner flow chart 152 and a cushion liner flow chart 164 according to the present disclosure. By using a fast-cure silicone material and a textile material arranged to cooperate with the fast-cure silicone material according to the disclosure, the pre-molding or coating process 151 may be entirely omitted, as there is no need to coat, cut, and shape a uniform tubular textile material to prevent bleed-through prior to the molding process. The prosthetic liner of the present disclosure greatly simplifies the costs and complexities of producing a prosthetic liner by reducing the process to a single molding process shown in flowcharts 152, 164, without the pre-molding steps required of existing or conventional sockets and liners.

To produce a locking liner according to locking-liner flowchart 152, a textile layer may be pre-molded at step 153, especially at the distal end, with a layer of silicone or other suitable material to facilitate support and use of a locking pin. The liner is then main-molded at step 154 with a fast-cure silicone material to form the inner layer without the need for any of the pre-coating processes of the pre-molding process 151 shown above dividing line 170.

The steps of the pre-molding process 151, including the steps of silicone mixing, coating, textile cutting, and sewing/ gluing are necessary in existing processes to prevent bleed-through of uncured silicone material through the textile material and to form a tubular textile into a suitable shape for a prosthetic liner, but are advantageously omitted through the use of a fast-cure silicone material and cooperating textile material according to the embodiments. Likewise, to produce a cushion liner according to cushion-liner flowchart 164, a textile layer may be main-molded at step 166 with a fast-cure silicone material to form an inner layer without the pre-coating processes of the pre-molding process 151 shown above the dividing line 170.

As seen in FIG. 1C, using a fast-cure silicone material to form an inner layer on a textile layer arranged to cooperate with the fast-cure silicone material reduces the cost and complexities of manufacturing as the majority of steps may be omitted entirely, and further allows for a wider variety of textile layers, including pre-formed tubular sleeves or socks, to be used, as it is no longer required to use a uniform tubular textile material to facilitate the coating step at step 151. The inner layer 101 may have a first thickness T1 and the textile layer 102 may have a second thickness T2, both thicknesses T1 and T2 suitable for use in a prosthetic liner and together defining a total thickness of the prosthetic liner 100. The thicknesses T1, T2 may be variable along a length or about a circumference of the prosthetic liner 100.

Figure 1E:
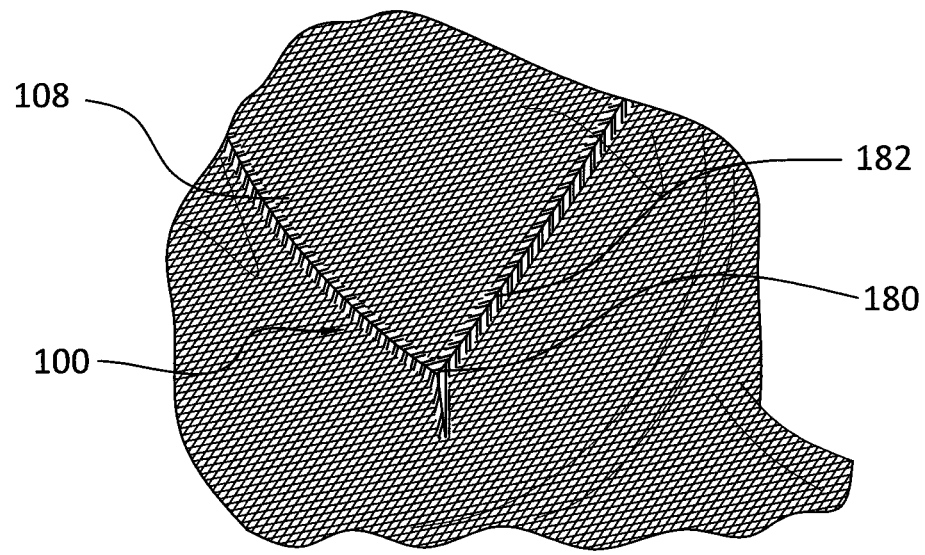
FIG. 1E is a perspective view of a distal portion of the prosthetic liner of FIG. 1A.

The textile layer 102 may be pre-formed and may have different distal closing configurations, as depicted in FIGS. 1D-1E. The closed distal end 180 shown in FIG. 1E may be formed as a Y-shaped seam 182, with branches spacing over the distal end 108 of the prosthetic liner 100. Alternatively in FIG. 1F, the distal closing 190 may be formed as an I-shaped seam 192, with a branch extending down a center portion of the distal end 108. The distal closings 180, 190 may be chosen in different prosthetic liners based on the desired configurations of the prosthetic liner 100, a corresponding prosthetic socket, and/or according to the needs of a particular user. The closed distal end 180, 190 is not limited to the depicted configurations and may be formed in any suitable or convenient shape or configuration.

Figure 2A:
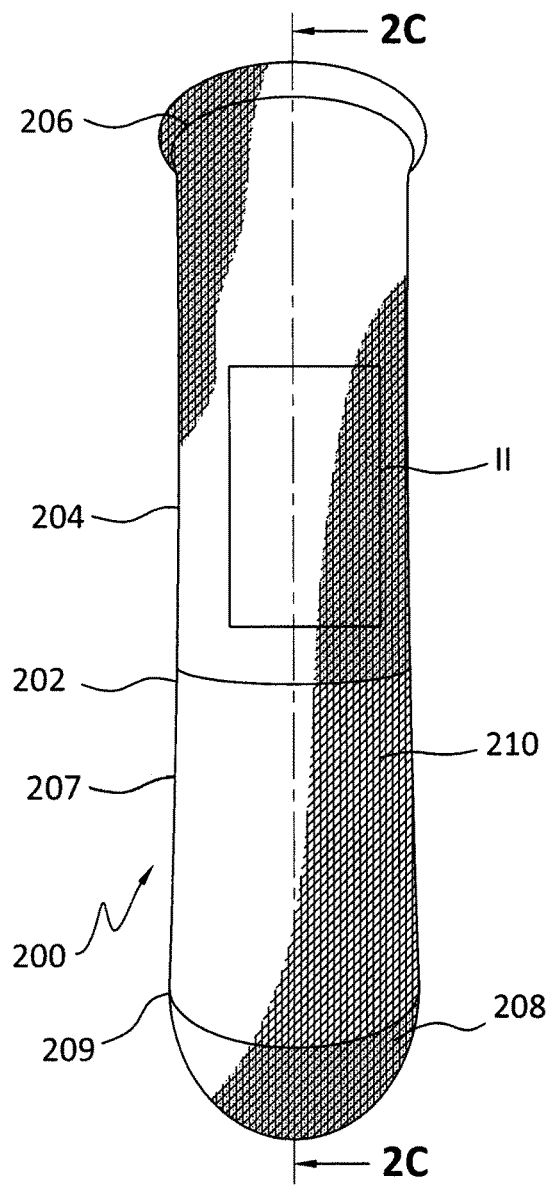
FIG. 2A is an elevational view of a prosthetic liner according to another embodiment of the disclosure.
Figure 2C:
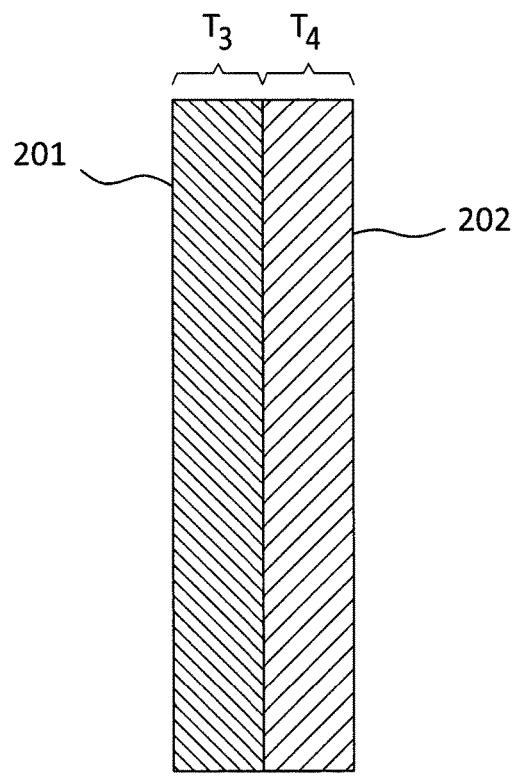
FIG. 2C is a cross-sectional view of the prosthetic liner of FIG. 2A taken along the line 2C-2C.
Figure 2B:
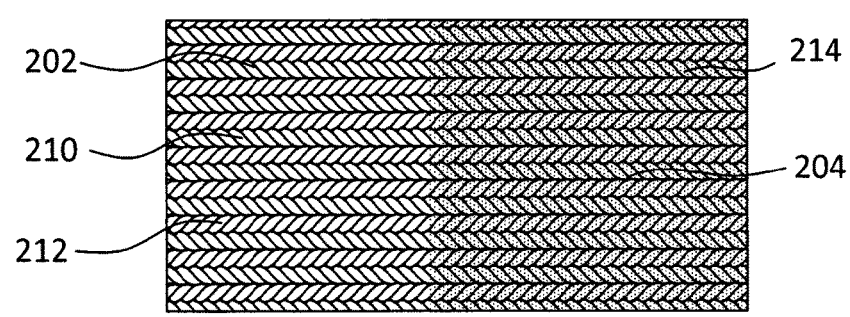
FIG. 2B is a detail view II of a textile material in the prosthetic liner of FIG. 2A.

Among the benefits of using a wider variety of textile materials to form the textile layer 102 according to the present disclosure is the possibility of including regions of distinct structures and functionality, such as a matrix, within a pre-formed textile material as shown in the embodiment of FIGS. 2A-2C. As shown, a prosthetic liner 200 may comprise an inner layer 201 and a textile layer 202 adjacent and attached thereto and comprising a textile material 204. The shape of the prosthetic liner 200 is defined by a distal seam 209 which discretizes a distal portion 208 and a body portion 210, which is also discrete from a proximal portion 206. The distal seam 209 may be provided as part of the textile sleeve 202 or may be added to the sleeve 202 during manufacturing. The material of the textile layer 202 may be different in the distal portion 208, the body portion 210, and/or the proximal portion 206 as suitable for a particular user or for a particular function. For instance, the textile layer 202 in the distal portion 208 may comprise nylon yarns, while the textile layer 202 in the body portion 210 may omit the nylon yarns in favor of a different material. Different sections having different materials may have different knit structures, or may have the same knit structure, such as jersey-knit gauge-19 yarns with terry.

Because of the provision of a fast-cure silicone material and cooperating textile material 204 which allow the inner layer 201 to be formed directly on the textile layer 202 without a pre-coating process and without bleed-through, the textile layer 202 may be provided in a pre-formed configuration and may include a matrix 207 defined by a material 212 comprising thermofusible yarns which may be configured to contribute added structure and stiffness in desired directions, such as axially, upon molding.

A matrix 207 may extend from the distal portion 208 up to a region of the body portion 210. A remainder of the body portion 210 may comprise a textile material 214 without the thermofusible yarns. As seen in FIG. 2B, the materials 212 and 214 may be defined within a single, continuous, and pre-formed textile sleeve 202, mitigating the need in existing or conventional prosthetic liners to cut, size, and stitch together materials, such as tubular textile materials, with different properties into a textile layer.

Figure 1F:
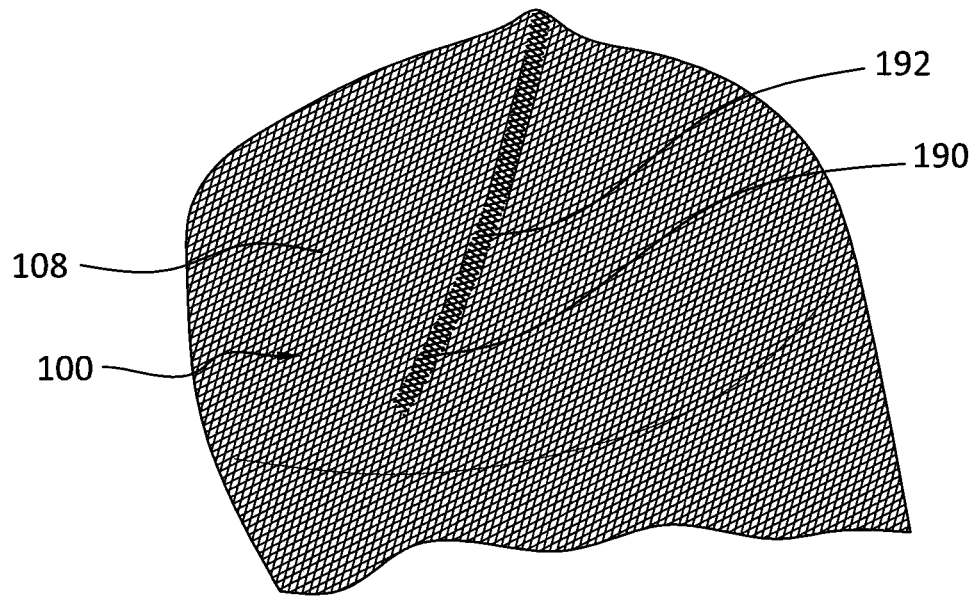
FIG. 1F is a perspective view of another embodiment of a distal portion of the prosthetic liner of FIG. 1A.

In embodiments, thermofusible yarns may be used to close the I- or Y-shaped seam 182, 192 shown in FIGS. 1E-1F, the thermofusible yarns serving to improve the adhesion and connection at the seam 182, 192 by fusing with adjacent yarns or threads when a threshold temperature has been met. The thermofusible yarns may be a low-temperature fusing yarn, such as a threshold of about 85° C., or may be a high-temperature fusing yarn, such as a threshold of about 110° C. to about 150° C., or any other suitable threshold. The thermofusible yarns of the seam 182, 192 may be provided in the textile sleeve or sock, or may be added during the manufacturing process.

As seen in cross-sectional view in FIG. 2C, the inner layer 201 may be formed directly adjacent to the textile layer 202 without a pre-coating inner layer interposed therebetween, as the fast-cure silicone material and cooperating textile layer of the disclosure allow for the omission of a pre-coating stage to prevent bleed-through. The inner layer 201 may have a first thickness T3, and the textile layer 202 may have a second thickness T4, with both thicknesses T3 and T4 suitable for use in a prosthetic liner 200 and defining a total thickness of the prosthetic liner 200. The thicknesses T3 and T4 may vary along a length or a circumference of the prosthetic liner 200 for added comfort at a distal end, for example, and/or for ease in donning/doffing the prosthetic liner 200.

Figure 3A:
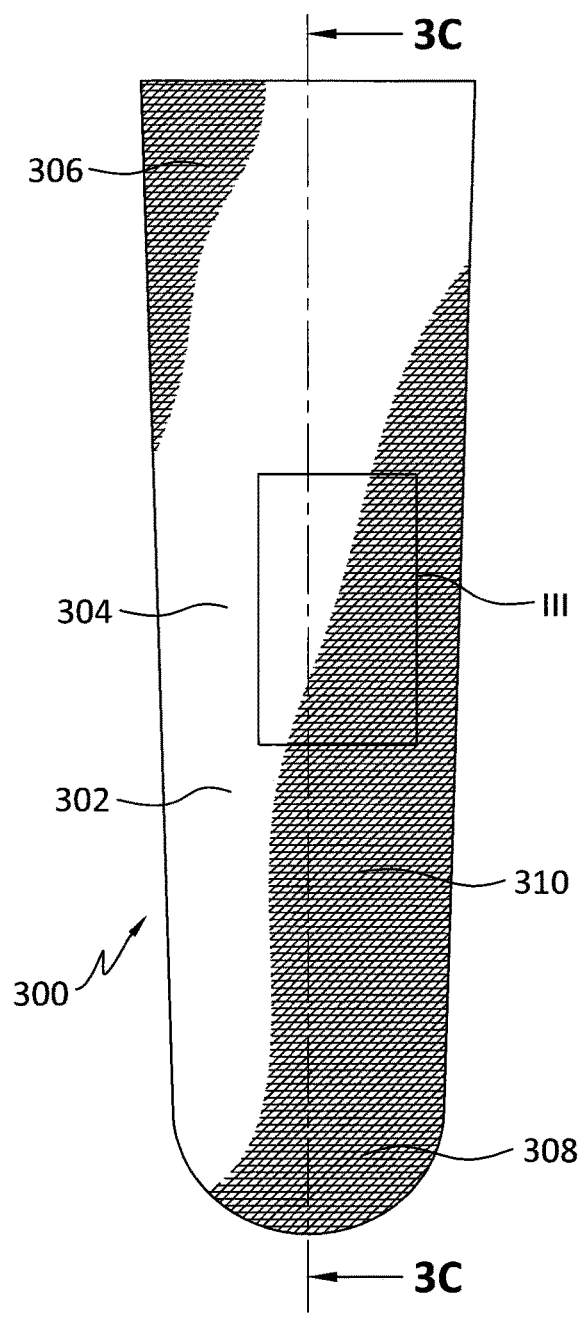
FIG. 3A is an elevational view of a prosthetic liner according to another embodiment of the disclosure.
Figure 3B:
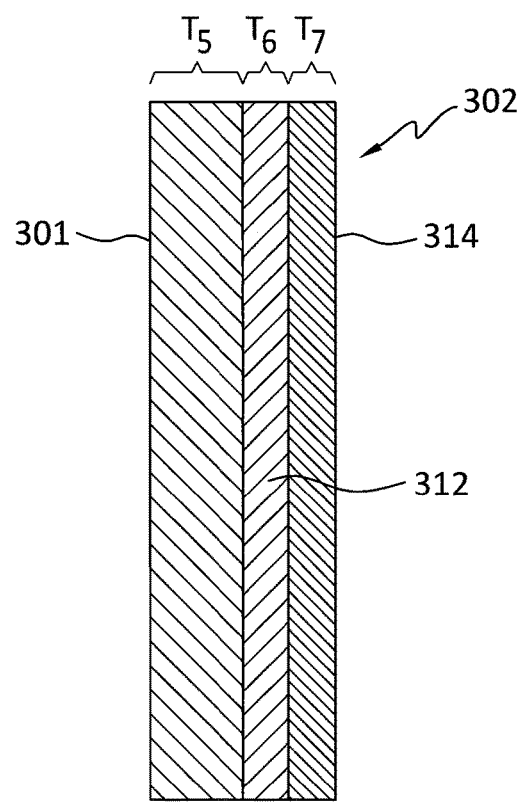
FIG. 3B is a cross-sectional view of the prosthetic liner of FIG. 3A taken along the line 3C-3C.
Figure 3C:
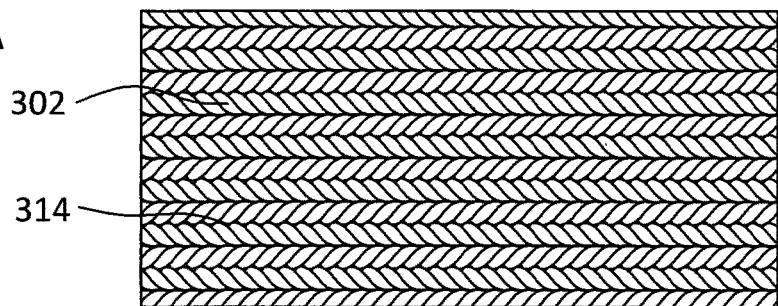
FIG. 3C is a detail view III of a textile material in the prosthetic liner of FIG. 3A.

FIGS. 3A-3C depict another embodiment of a prosthetic liner 300 according to the present disclosure. A prosthetic liner 300 comprises an inner layer 301 and a textile layer 302 adjacent and attached to the inner layer 301. Similar to the previously depicted embodiment of FIG. 2A-2C, the prosthetic liner 300 may define a continuous body portion 310 defined between a proximal portion or end 306 and a distal portion or end 308.

The textile layer 302 may advantageously comprise multiple layers of altogether different materials and knit structures. An inner or base yarn 312 adjacent to the inner layer 301 may comprise a first yarn type, and an outer or covering yarn 314 adjacent and attached to the inner yarn 312 may comprise a different second yarn type. The base and covering yarns 312, 314 may have properties suitable for their respective positions. The inner layer 301 may have a first thickness T5, while the base yarn 312 has a second thickness T6 and the covering yarn 314 has a third thickness T7, the thicknesses T5, T6, T7 defining a thickness of the prosthetic liner 300, which, as before, may be continuous or may vary at different locations of the liner 300. The covering yarn 314 may have different elongation, axially or radially, compared to the base yarn 312.

The base yarn 312 may have a knit structure and material arranged to interlock on an inner surface thereof with the fast-cure silicone material of the inner layer 301 to ensure a firm attachment between the inner layer 301 and the textile layer 302. The covering yarn 314 may be arranged with a knit structure and material 314 configured for aesthetic appeal, enhanced comfort, and/or optimal attachment to a prosthetic socket. As in previous embodiments, the layers 312, 314 of the textile layer 302 may be arranged to cooperate with the fast-cure silicone material to prevent bleed-through, allowing for a simplified manufacturing process and the use of advanced and/or customized textile materials. The properties of the base yarn 312 and the covering yarn 314, for instance, may be varied about or along the liner 300 as appropriate for providing desired shapes, elasticities, cushioning, or friction properties, for example.

In an embodiment, the base yarn 312 may comprise a different material than the material of the covering yarn 314. The base yarn 312 may comprise a jersey-knit gauge-19 uncovered nylon material without terry, while the covering yarn 314 may comprise a jersey-knit gauge-19 elastane. In other non-limiting embodiments, the base yarn 312 may comprise a jersey-knit gauge-19 elastane, while the covering yarn 314 comprises a jersey-knit gauge-19 elastane having a different density. In yet other embodiments, the base yarn 312 may comprise a pique-knit gauge-24 elastane, while the covering yarn 314 may comprise a pique-knit gauge-24 elastane comprising tencel threads.

The base yarn 312 may comprise low-melt thermal yarns or threads, particularly in the distal end portion 308 of the liner 300. The low-melt threads, which may be configured to melt and fuse with adjacent threads at approximately 85° C., may define a matrix extending approximately 12 inches from the distal end portion 308 into the body portion 310 of the liner 300. The body portion 310 extending proximally from the distal end portion 308 may have a different composition of base yarn 312 and covering yarn 314.

While the depicted embodiment shows the base yarn 312 and the covering yarn 314 extending throughout the textile layer 302, it will be appreciated that the base yarn 312 and the covering yarn 314 may extend only through discrete portions of the textile layer 302 and may vary at different locations. For example, a distal end portion 308 of the liner 300 may have a different base yarn and covering yarn arrangement than a body portion 310 of the liner 300.

Another advantage of the present disclosure is depicted in the prosthetic liner 400 of FIGS. 4A-4D. Using a fast-cure silicone material to form the inner layer 401, and a textile layer 402 arranged to cooperate with the fast-cure silicone material to prevent bleed-through, facilitates the use of a textile material 404 that may be pre-formed with features, such as discrete bands or regions of different material properties, that would be cumbersome if not impossible to provide using conventional techniques. In the depicted embodiment, the discrete regions may provide alternating or periodic bands 422 in the textile layer 402. The bands 422 may comprise coarse inelastic textile that allows for uncured silicone material to bleed through an entirety of a thickness thereof to define silicone seal-in bands 420, and bands 414 of dense, fine, elastic textile material that does not permit bleed-through of uncured silicone material. These bands 414 define regions 412 of non-bleed textile material 404. A body portion 410 may be distinct from a proximal end 406 and a distal portion 408, with the distal portion 408 devoid of the different bands 422, 414. The distal portion 408 may comprise any of the bands 414 or 420 so as to allow bleed-through (where desired) or to prevent bleed-through (where desired). The bands 422 may have different elongation, axially or radially, compared to the bands 414.

By providing the bands or zones 422, the seal-in bands 420 may be provided on discrete and desired regions of an outer or socket-facing surface of the prosthetic liner 400 to interface with the socket, such as for vacuum-sealing, for donning/doffing purposes, and/or for rotational control between the liner 400 and the socket. The provision of the zones 422 in a pre-formed textile layer or sleeve 402 further simplifies the manufacturing process without compromising needed structural properties. While the seal-in bands 420 are shown as extending laterally around band-like portions of the prosthetic liner 400, it will be understood that any configuration, size, quantity, and/or pattern of controlled bleed-through sections 422 may be defined by the textile layer 402 for desired properties, such as tackiness and texture, breathability, shape, stiffness, cushioning, or otherwise.

Figure 4A:
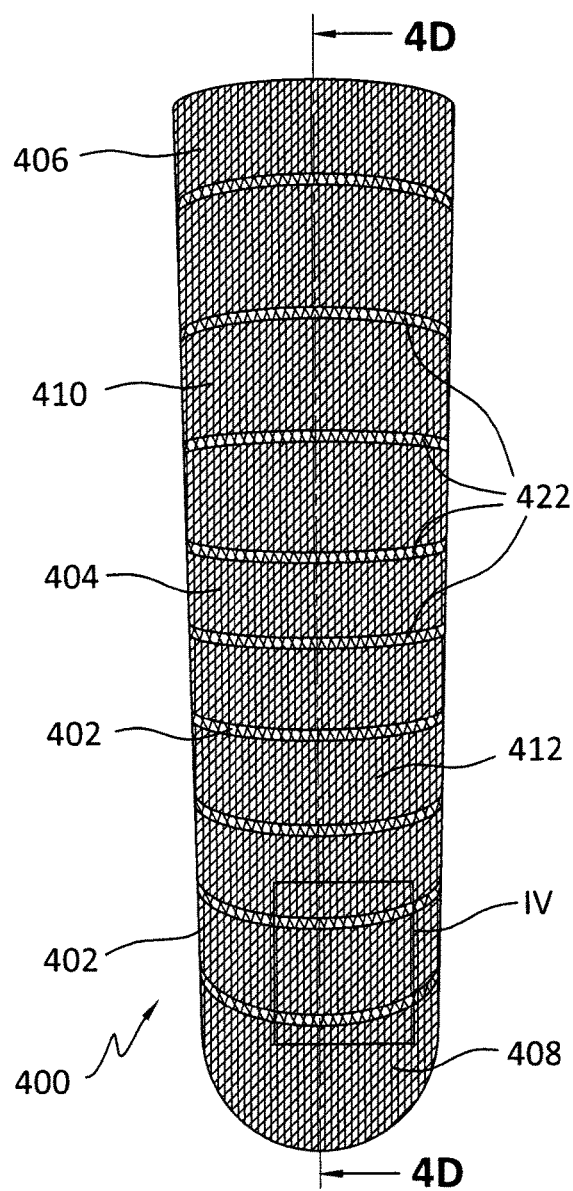
FIG. 4A is an elevational view of a prosthetic liner according to another embodiment of the disclosure.
Figure 4B:
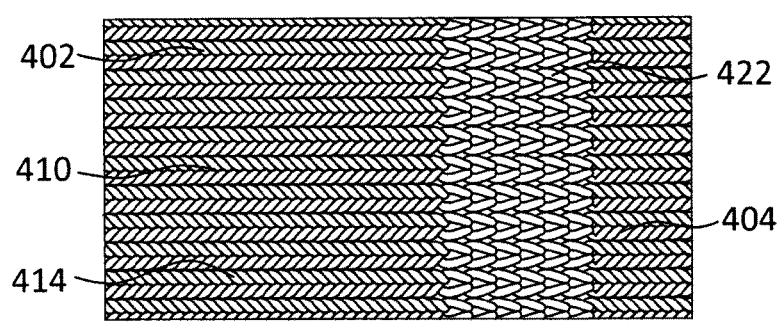
FIG. 4B is a detail view IV of a textile material in the prosthetic liner of FIG. 4A.
Figure 4D:
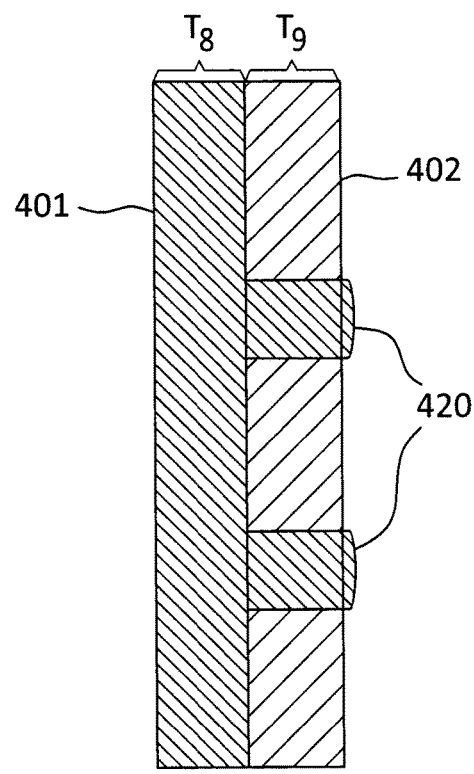
FIG. 4D is a cross-sectional view of the prosthetic liner of FIG. 4A taken along the line 4D-4D.
Figure 4C:
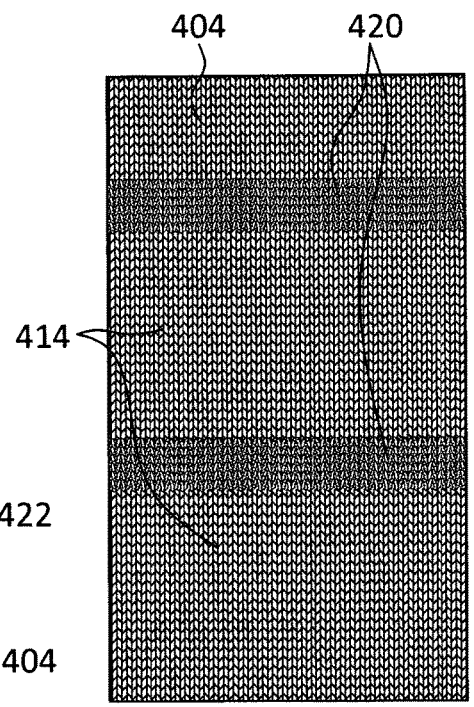
FIG. 4C is a detail view IV of a textile material after the inner layer has been applied to the textile material of FIG. 4B.

As seen in greater detail in the cross-sectional view of FIG. 4D, the inner layer 401 may be arranged to directly abut and attach to the textile layer 402, with portions of uncured silicone material bleeding through the bands 422 to define seal-in bands 420 that extend to an outer surface of the prosthetic liner 400 at desired and discrete locations. The inner layer 401 may have a first thickness T8 and uncured silicone material may bleed through an entire thickness T9 of the textile layer 402, with the thicknesses T8, T9 defining substantially an entire thickness of the prosthetic liner 400. Portions of silicone forming the seal-in bands 420 may extend a distance beyond the outer surface of the textile layer 402 or may be flush with the outer surface of the textile layer 402.

The bands 422 may be arranged to allow bleed-through of uncured silicone material by defining portions of the textile material 404 whereat a predetermined number of threads, filaments, or other patterns that define the textile material 404 are skipped or omitted. Alternatively, the density, gauge, material type, or any other property of the textile material can be varied as desired to facilitate controlled bleed-through. This arrangement provides regions 422 of reduced density that facilitate bleed-through by and of the uncured silicone material before the silicone cures.

The textile material 404 may be arranged to be denser throughout the main body of the textile layer 402 than an existing tubular textile layer, such that bleed-through of uncured silicone is prevented. The predetermined number of omitted threads at bands 422 facilitate a lower density conducive to bleed-through and the formation of seal-in bands 420 or other features. The bands 422 may also be provided for desired elasticity properties.

Like the matrix of thermofusible yarns embedded in the pre-formed textile sleeve 202 of the embodiment depicted in FIGS. 2A-2B, the textile layer 402 may be pre-formed, in contrast to the tubular textile structures of existing or conventional liners which must be painstakingly cut, sized, and adhered together. To provide a smoother profile and an improved sealing of the uncured silicone material, the textile layer 402 may be arranged with a closing seam at the distal end 408 with a low-melt yarn. This arrangement provides for improved sealing while also providing an expedited and simplified manufacturing process. As with previous embodiments, the textile layer 402 may define base and covering layers or a single layer of fabric, and may have uniform properties throughout or varied properties at different locations.

Figure 5A:
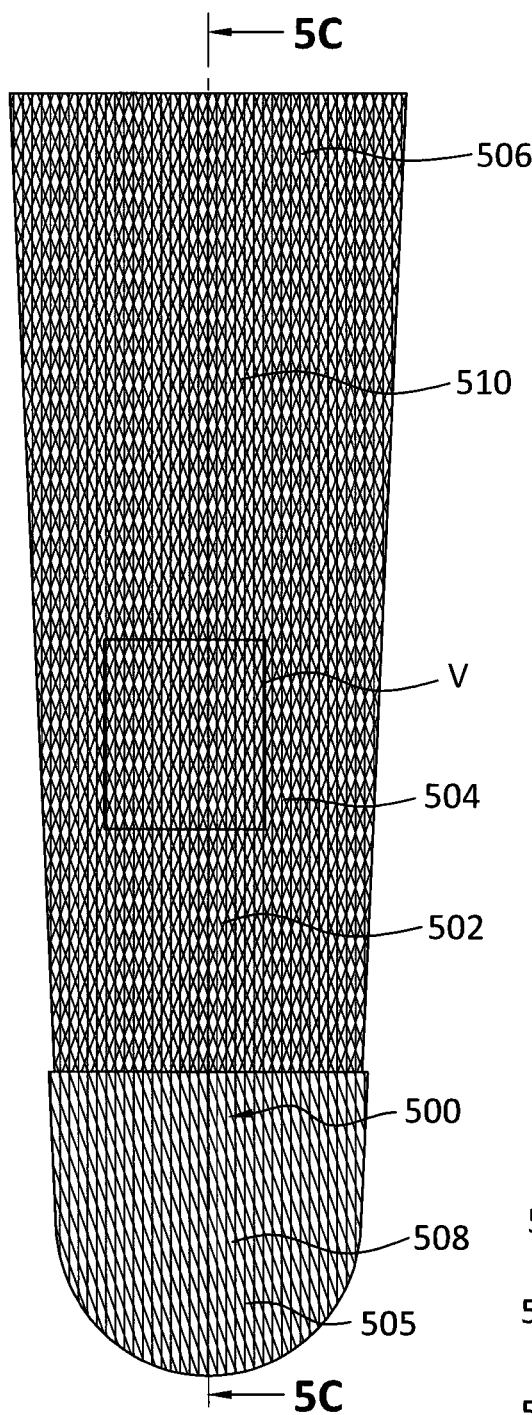
FIG. 5A is an elevational view of a prosthetic liner according to another embodiment of the disclosure.
Figure 5C:
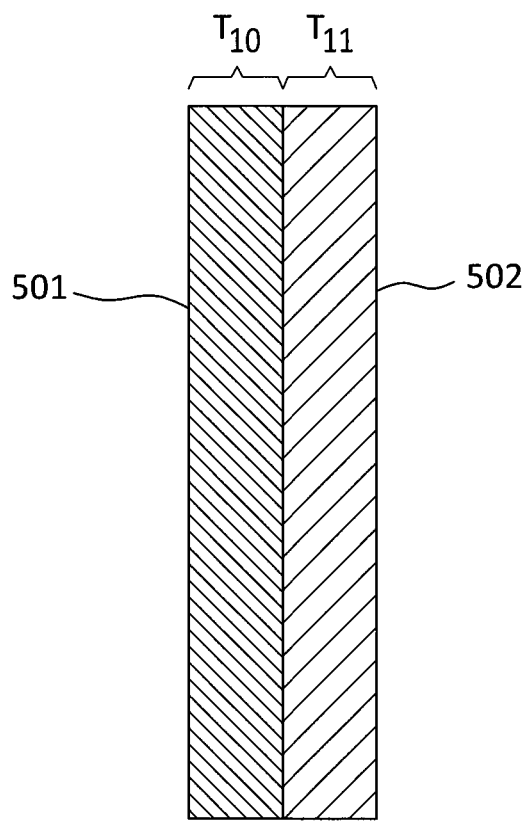
FIG. 5C is a cross-sectional view of the prosthetic liner of FIG. 5A taken along the line 5C-5C.
Figure 5B:
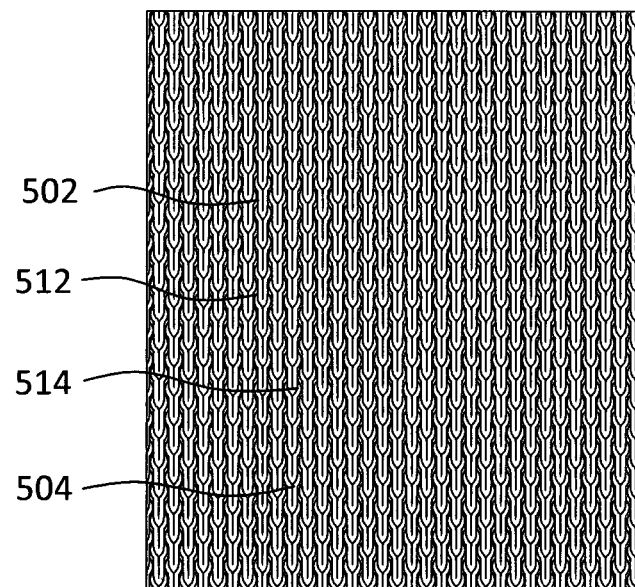
FIG. 5B is a detail view V of a textile material in the prosthetic liner of FIG. 5A.

The prosthetic liner 500 according to the embodiment of FIGS. 5A-5C further demonstrates the advantages of the present disclosure. As with the foregoing embodiments, by forming the inner layer 501 from a fast-cure silicone material that cooperates with a textile layer 502 arranged to prevent bleed-through of the uncured silicone material, a pre-coating process may be omitted entirely, and the textile layer 502 may be a pre-formed material with added structural and functional properties compared to existing textiles used in prosthetic liners.

A pre-formed textile layer 502 may comprise different materials in a body portion 510 compared to a distal portion 508, which is located on an opposite end of the prosthetic liner 500 from a proximal portion or end 506. The body portion 510 may comprise a first textile material 504, and the distal portion 508 may comprise a second textile material 505. The first textile material 504 may define a two-system textile, with a first system 512 comprising, for example, two yarns of polyester or polyamide material in a 1 by 1 alternating knit structure, and a second system 514 comprising, for example, one yarn of a premium-stretch fiber, with the first and second systems 512 and 514 in a knitted and/or alternating arrangement with each other. The first textile material 504 is depicted in greater detail in FIG. 5B.

In an alternative embodiment, the first material 504 may comprise a single system, which may comprise two yarns in a 1 by 1 alternating knit structure. It will be understood that the first and second textile materials 504, 505, and the first and second systems 512, 514 may comprise other types of knit structures and materials and may vary from the depicted embodiment in number of yarns, number of layers, stitching patterns, and other details. The provision of the first and second textile materials 504, 505 may advantageously allow for desired properties at desired locations, such as different elasticities at different portions of a user's anatomy, different stiffness, better rotation control relative to the socket, increased cushioning at particular portions, or otherwise.

By providing a fast-cure silicone material with a cooperating textile layer 502 according to the present disclosure, the textile layer 502 may comprise the above-mentioned discrete zones of different material, such as in the distal end portion 508 and in the body portion 510, to serve different structural needs. Greater thickness, padding and comfort can be provided in the distal portion 508 with greater breathability or frictional engagement with a socket provided in the body portion 510.

In other embodiments, the first textile material 504 may define regions of high stretch and elasticity, which may be advantageous for providing flexibility over a joint. Regions of reduced stretch or increased stiffness may be provided for, e.g., a popliteal region, so as to prevent discomfort and bunching. Advantageously, the textile layer 502, with the first and second textile materials 504, 505, may be pre-formed, eliminating the need to cut, size, and stitch or otherwise glue together portions of different materials after a pre-coating process as in existing or conventional liners.

Similar to previously depicted embodiments, the inner layer 501 and the textile layer 502 of the prosthetic liner 500 may have respective first and second thicknesses T10, T11, which may be constant or dynamic over a length of the prosthetic liner 500, and which together define a thickness of the prosthetic liner 500. By utilizing a fast-cure silicone material according to the disclosure, the inner layer 501 may be formed directly on the textile layer 502 without the need for a separate layer of silicone pre-coating on the textile layer 502 to prevent bleed-through of uncured silicone material and without compromising a required thickness at portions of the prosthetic liner 500. For example, the inner layer 501 may be thicker at the distal end 508 for added cushioning.

Figure 6A:
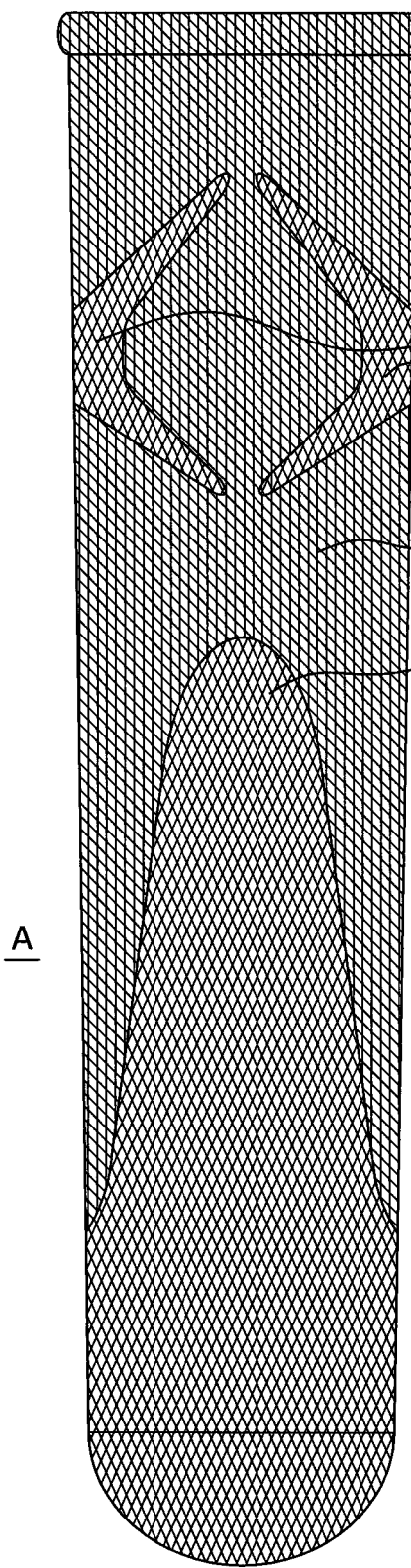
FIG. 6A is an elevational view of a front side of a textile sleeve according to another embodiment of the disclosure.
Figure 6B:
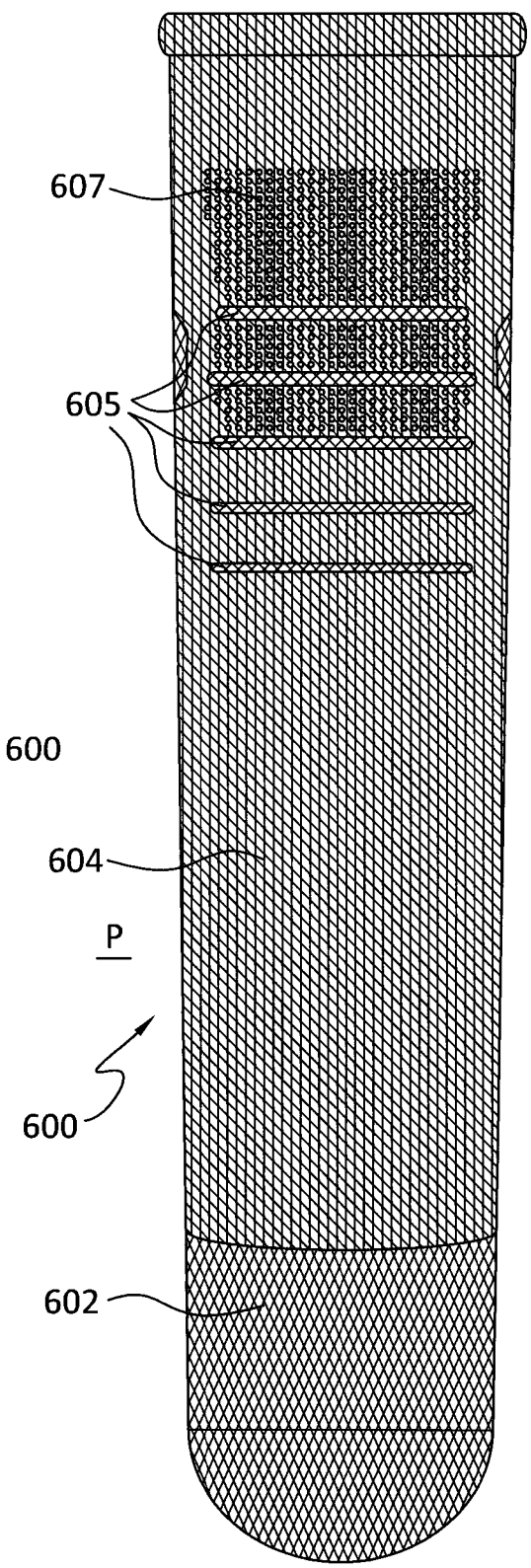
FIG. 6B is an elevational view of a rear side of the textile sleeve of FIG. 6A.

Another embodiment of a textile layer arranged to cooperate with the fast-cure silicone material of the disclosure is shown in an elevational view in FIGS. 6A-6B. FIG. 6A shows a front or anterior side A of a textile layer that may be formed as a textile sleeve or sock 600 having distinct, particular regions having different advantageous properties, the provision of which in existing tubular and/or open-ended textile materials is cumbersome and costly owing to the cutting, shaping, and stitching stages required to provide different regions from different materials. By contrast, the textile sleeve 600 may be pre-formed with the particular regions, requiring no such cutting, shaping, and stitching stages prior to curing with a fast-cure silicone material. A distal portion of the textile sleeve 600 may be formed from a low-stretch portion 602, the low-stretch portion 602 configured to limit axial stretching and thereby minimize pistoning in a prosthetic system.

Proximal and attached to the distal portion of the textile sleeve 600 is a high-stretch portion 604, configured to facilitate axial stretching of a prosthetic liner. This may be particularly advantageous for allowing a user to bend their knee, for example, with minimized resistance from the prosthetic liner and may facilitate donning and doffing of the prosthetic liner. The high-stretch portion 604 may extend toward a proximal portion of the textile sleeve or sock 600. The high-stretch portion 604 may define a region or regions having stiffened material relative to a remainder of the high-stretch portion 604, the stiffened material forming a patella support 610. The patella support 610 may be arranged to substantially surround and support a patella during flexion and extension of the limb residuum, with the enhanced stiffness of the patella support 610 helping to maintain the patella in its proper position and apply desired amounts of pressure thereto.

On a rear or posterior side P of the textile sleeve 600 shown in FIG. 6B, a pattern of fold lines 605 may be provided proximate a popliteal region of a user in the form of softer yarns, the softer yarns facilitating folding at desired locations during flexion of the knee. The yarns at the fold lines 605 may also be thinner than a remainder of the textile sleeve 600. This advantageously can reduce bunching and associated discomfort (including moisture buildup and reduced breathability) in the popliteal region during use. More or fewer fold lines 605, and different configurations and constructions thereof, may be provided as suitable for a particular application or use, and are not limited to the depicted arrangement.

Discrete regions, in the depicted embodiment taking the form of a plurality of dots 607 of material, may be provided in the textile sleeve 600 and may have lighter (e.g. less dense) knitting to facilitate breathability particularly in the popliteal region over which the dots 607 are arranged. The dots 607 may define patterns corresponding to regions requiring greater heat-transfer characteristics. In other embodiments, the dots 607 having lower density may be provided to control or facilitate bleed-through of the fast-cure silicone material, the silicone features defined over the dots 607 on an exterior or socket-facing surface of the prosthetic liner providing rotation-control effects or other desired properties. The dots 607 may have any configuration or be provided in any number or pattern necessary, and are not limited to the depicted configuration and pattern.

The use of the fast-cure silicone material allows for the use of the textile sleeve 600, which may be pre-formed, with its distinct regions 602, 604, 610, 605, 607 having distinct characteristics that provide advantageous structures and functions to a prosthetic liner, without the cumbersome and costly steps of pre-coating, cutting, shaping, and stitching distinct portions of different materials having the desired properties, these steps precluding the use of textile sleeves in existing prosthetic liner manufacturing processes. The fast-cure silicone material and cooperating textile material of the disclosure thereby further reduce the costs and complexities of manufacturing while providing a superior prosthetic liner that better corresponds to a particular user's needs.

The prosthetic liner according to the disclosed embodiments advantageously streamlines and simplifies the manufacturing process for a prosthetic liner by providing a fast-cure silicone material that forms an inner layer with a textile layer arranged to cooperate with the fast-cure silicone material to prevent bleed-through of the uncured silicone material. The prevention of bleed-through by the fast-cure silicone material and the cooperating textile layer allows for the omission of the steps of silicone pre-mixing, coating, cutting, and sewing prior to molding or curing the prosthetic liner, and therefore allow for pre-formed textile layers, which may define numerous structural and functional properties.

It is to be understood that not necessarily all objects or advantages may be achieved under any embodiment of the disclosure. Those skilled in the art will recognize that the prosthetic liner and methods for making the same may be embodied or carried out in a manner that achieves or optimizes one advantage or group of advantages as taught herein without achieving other objects or advantages as taught or suggested herein.

The skilled artisan will recognize the interchangeability of various disclosed features. Besides the variations described herein, other known equivalents for each feature can be mixed and matched by one of ordinary skill in this art to construct a prosthetic liner and to utilize a method for making the same under principles of the present disclosure. It will be understood by the skilled artisan that the features described herein may be adapted to other types of prosthetic, orthopedic, medical, or other devices.

Although this disclosure describes certain exemplary embodiments and examples of an elastomeric prosthetic liner, it will be understood by those skilled in the art that the present disclosure extends beyond the specifically disclosed elastomeric prosthetic liner embodiments to other alternative embodiments and/or uses of the disclosure and obvious modifications and equivalents thereof, including liners formed from other polymeric materials and in other configurations. It is intended that the present disclosure should not be limited by the disclosed embodiments described above and may be extended to other applications that may employ the features described herein.

The invention claimed is:

1. A liner for prosthetic use, the liner having an exterior surface and an inner cavity forming an interior surface of the liner, the liner defining proximal and distal ends along a central longitudinal axis, the liner comprising:
   a textile sleeve having a first knit structure with interstices between yarns of said first knit structure, the textile sleeve defining an inner surface and an outer surface on an opposite side of the inner surface;
   a silicone material provided on the inner surface of the textile sleeve and impregnating the interstices of the first knit structure of the textile sleeve, the silicone material curable to at least 90% crosslinking within a range of about 120 to 210 seconds;
   wherein the silicone material impregnates only the inner surface of the textile sleeve, the outer surface devoid of the silicone material;
   wherein the silicone material forms an inner layer of the liner, the inner layer forms the interior surface of the liner and the outer surface of the textile sleeve forms the exterior surface of the liner, wherein a thickness of the liner from the interior surface of the liner to the inner surface of the textile sleeve consists of the silicone material of the inner layer;

wherein the first knit structure is selected from the group consisting of jersey and pique;

wherein the textile sleeve further comprises a second knit structure comprising a plurality of circumferential bands formed by a coarser knit than the first knit structure.

2. The liner of claim 1, wherein the first knit structure is of a jersey knit.

3. The liner of claim 1, wherein the first knit structure includes a taslanized or air-textured yarn.

4. The liner of claim 1, wherein the textile sleeve includes at least one distal portion forming a closed end and a matrix portion extending from the at least one distal portion, the at least one distal portion and the matrix portion comprising thermofusible yarns.

5. The liner of claim 4, wherein the textile sleeve comprises a body portion extending from the matrix to a proximal end forming an open end to the textile sleeve, the body portion being devoid of the thermofusible yarns.

6. The liner of claim 1, wherein the second knit structure comprises an inelastic knit structure and is arranged for the silicone material to extend through the second knit structure from the inner surface to the outer surface of the textile sleeve.

7. The liner of claim 1, wherein the textile sleeve defines at least one more knit structure connected to the first knit structure, the at least one more knit structure having a different knit structure than the first knit structure including different axial or radial elongation.

8. The liner of claim 1, wherein the inner layer has a thickness in the range of 1 to 15 mm and the textile sleeve has a thickness of 0.75 to 2 mm.

9. The liner of claim 1, wherein the silicone forms an entirety of the interior surface of the inner cavity of the liner.

10. A liner for prosthetic use, the liner having an exterior surface and an inner cavity forming an interior surface of the liner, the liner defining proximal and distal ends along a central longitudinal axis, the liner comprising:

a textile sleeve having a first knit structure with interstices between yarns of said first knit structure, the textile sleeve defining an inner surface and an outer surface on an opposite side of the inner surface;

a silicone material provided on the inner surface of the textile sleeve and impregnating the interstices of the first knit structure of the textile sleeve, the silicone material curable to at least 90% crosslinking within a range of about 120 to 210 seconds;

wherein the silicone material impregnates the inner surface of the textile sleeve;

wherein the silicone material forms an inner layer of the liner, the inner layer forms the interior surface of the liner and the outer surface of the textile sleeve forms the exterior surface of the liner, wherein a thickness of the liner from the interior surface of the liner to the inner surface of the textile sleeve consists of the silicone material of the inner layer;

wherein the first knit structure is selected from the group consisting of jersey and pique;

wherein the textile sleeve forms bands defined by an inelastic textile through which the silicone material bleeds through an entirety of a thickness of the textile sleeve and defines silicone seal-in bands along the exterior surface of the liner.

11. The liner of claim 10, wherein the textile sleeve defines dense textile material between the bands arranged to prohibit bleed-through by silicone material.

12. The liner of claim 10, wherein the distal end of the textile sleeve is devoid of the bands.

13. The liner of claim 10, wherein the seal-in bands extend a distance beyond the exterior surface of the textile sleeve.

14. The liner of claim 10, wherein the textile sleeve includes at least one distal portion forming a closed end and a matrix portion extending from the at least one distal portion, the at least one distal portion and the matrix portion comprising thermofusible yarns.

15. The liner of claim 14, wherein the textile sleeve comprises a body portion extending from the matrix to a proximal end forming an open end to the textile sleeve, the body portion being devoid of the thermofusible yarns.

16. The liner of claim 10, wherein the textile sleeve further comprises a second knit structure comprising a plurality of circumferential bands formed by a coarser knit than the first knit structure.

* * * * *